US011459623B2

(12) United States Patent
Melard et al.

(10) Patent No.: US 11,459,623 B2
(45) Date of Patent: Oct. 4, 2022

(54) IN VITRO METHOD FOR DETECTING AND QUANTIFYING HIV-2 DNA

(71) Applicants: UNIVERSITE PARIS DESCARTES, Paris (FR); INSTITUT NATIONAL DE LA SANTE ET DE LA RECHERCHE MEDICALE, Paris (FR); ASSISTANCE PUBLIQUE-HOPITAUX DE PARIS, Paris (FR); UNIVERSITE PARIS DIDEROT, Paris (FR); UNIVERSITE PARIS NORD, Villetaneuse (FR); UNIVERSITE DE ROUEN, Mont-Saint-Aignan (FR); CHU DE ROUEN, Rouen (FR)

(72) Inventors: Adeline Melard, Morangis (FR); Mélanie Bertine, Bretigny sur Orge (FR); Véronique Avettand Fenoel, Paris (FR); Florence Damond, Saint Mande (FR); Christine Rouzioux, Paris (FR); Diane Descamps, Paris (FR); Marie Gueudin, Rouen (FR); Jean-Christophe Plantier, Bois-Guillaume (FR)

(73) Assignees: UNIVERSITÉ PARIS CITÉ, Paris (FR); ASSISTANCE PUBLIQUE-HOPITAUX DE PARIS, Paris (FR); CHU DE ROUEN, Rouen (FR); INSTITUT NATIONAL DE LA SANTE ET DE LA RECHERCHE MEDICALE, Paris (FR); UNIVERSITE DE ROUEN, Mont-Saint-Aignan (FR); UNIVERSITÉ PARIS NORD, Villetaneuse (FR)

( * ) Notice: Subject to any disclaimer, the term of this patent is extended or adjusted under 35 U.S.C. 154(b) by 188 days.

(21) Appl. No.: 16/611,000

(22) PCT Filed: May 4, 2018

(86) PCT No.: PCT/EP2018/061624
§ 371 (c)(1),
(2) Date: Nov. 5, 2019

(87) PCT Pub. No.: WO2018/202904
PCT Pub. Date: Nov. 8, 2018

(65) Prior Publication Data
US 2020/0080160 A1 Mar. 12, 2020

(30) Foreign Application Priority Data
May 5, 2017 (FR) ..................................... 1753969

(51) Int. Cl.
C12P 19/34 (2006.01)
C12Q 1/70 (2006.01)

(52) U.S. Cl.
CPC ......... *C12Q 1/703* (2013.01); *C12Q 2600/16* (2013.01)

(58) Field of Classification Search
CPC ...................................................... C12Q 1/703
See application file for complete search history.

(56) References Cited

U.S. PATENT DOCUMENTS

| 10,385,410 B2 * | 8/2019 | Rouzioux | ................ C12Q 1/68 |
| 2012/0283131 A1 * | 11/2012 | Biron | .................... C12Q 1/703 506/9 |

(Continued)

FOREIGN PATENT DOCUMENTS

WO 2015181627 A1 12/2015

OTHER PUBLICATIONS

Avettand-Fenoel Veronique et al. "New sensitive one-step real-time duplex PCR method for group A and B HIV-2 RNA load", Journal of Clinical Microbio., pp. 3017-3022, vol. 52, No. 8, (Aug. 2014).

(Continued)

*Primary Examiner* — Kenneth R Horlick
(74) *Attorney, Agent, or Firm* — Browdy and Neimark, PLLC (57) ABSTRACT

The present invention relates to a method for detecting or quantifying deoxyribonucleic acid (DNA) of human immunodeficiency virus 2 (HIV-2) in a sample containing DNA comprising: a) performing a real-time polymerase chain reaction (PCR) on the sample, or a fraction thereof comprising DNA, with at least two sets of primers and probe each respectively comprising two primers and a labeled probe for the detection or quantification of HIV-2 DNA, at least one of the sets is selected from the group consisting of: a set comprising a primer comprising or consisting of a sequence SEQ ID NO: 1 or a sequence having al least 90% identity to SEQ ID NO: 1, a primer comprising or consisting of a sequence SEQ ID NO: 2 or a sequence having 90% identity to SEQ ID NO: 2 or the complement of these sequences, and a labeled probe comprising or consisting of a sequence SEQ ID NO: 3, or a sequence having at least 90% identify to SEQ ID NO: 3 or the complement of these sequences, and a set comprising a primer comprising or consisting of a sequence SEQ ID NO: 4 or a sequence having at least 90% identity to SEQ ID NO: 4, a primer comprising or consisting of a sequence SEQ ID NO: 5 or a sequence having 90% identity to SEQ ID NO: 5 or the complement of these sequences, and a labeled probe comprising or consisting of a sequence SEQ ID NO: 6 or a sequence having at least 90% identity to SEQ ID NO: 6 or the complement of these sequences, and b) determining therefrom the presence or absence and/or the quantity of HIV-2 DNA in the biological sample.

12 Claims, 3 Drawing Sheets
Specification includes a Sequence Listing.

(56) References Cited

U.S. PATENT DOCUMENTS

| | | | |
|---|---|---|---|
| 2014/0248306 A1* | 9/2014 | Charneau | A61P 35/00 424/199.1 |
| 2017/0218467 A1* | 8/2017 | Rouzioux | C12Q 1/68 |

OTHER PUBLICATIONS

Avettand-Fenoel Veronique et al.. "LTR Real-Time PCR for HIV-1 DNA Quantitation in Blood Cells for Early Diagnosis in Infants Born to Seropositive Mothers Treated in HAART Area (ANRS CO 01)", Journal of Medical Virology, pp. 217-223, vol. 81, (Feb. 2009).

Behrendt R. et al., "A neutralization assay for HIV-2 based on measurement of provirus integration by duplex real-time PCR", journal of Virological Methods, pp. 40-46, vol. 159 (Feb. 2009).

Melanie Bertine et al., "New Highly Sensitive Real-Time PCR Assay for HIV-2 Group A and Group B DNA Quantification", Journal of Clinical Microbiology, pp. 2850-2857, vol. 55, No. 9, (Sep. 2017).

Charpentier et al., "Genotypic resistance profiles of HIV-2-treated patients in West Africa", AIDS, pp. 1161-1169, vol. 28, No. 8 (May 2014).

Damond F. et al. "Quantification of proviral load of human immunodeficiency virus type 2 subtypes A and B using real-time PCR" Journal of Clinical Microbiology, pp. 4264-4268, vol. 39, No. 12 (Dec. 2001).

Damond F. et al., "Improved Sensitivity of Human Immunodeficiency Virus Type 2 Subtype B Plasma Viral Load Assay", Journal of Clinical Microbiology, pp. 4234-4236, vol. 43, No. 8 (Aug. 2005).

Dehee A. et al.,"Quantification of Epstein-Barr Virus Load in Peripheral Blood of Human ImmunodeJournal of Medical Virologyciency Virus-Infected Patients Using Real-Time PCR", Journal of Medical Virology, pp. 543-552, vol. 65 (Oct. 2001).

Dib et al., "A comprehensive genetic map of the human genome based on 5,264 microsatellites" Nature, pp. 152-154, vol. 380 (Mar. 1996).

Gueudin et al., "Quantification of Proviral DNA Load of Human Immunodeficiency Virus Type 2 Subtypes A and B Using Real-Time PCR", Methods in Molecular Biology, pp. 215-220, (2005).

Gueudin et al., "Differences in proviral DNA load between HIV-1- and HIV-2-infected patients", AIDS, pp. 211-215, vol. 22, (Jan. 2008).

Holland et al., "Detection of specific polymerase chain reaction product by utilizing the 5'-3' exonuclease activity of Thermus aquaticus DNA polymerase", Proc. Natl. Acad. Sci. USA, pp. 7276-7280, vol. 88 (Aug. 1991).

Ahsen et al., "Rapid Detection of Prothrombotic Mutations of Prothrombin (G20210A), Factor V (G1691A), and Methylenetetrahydrofolate Reductase (C677T) by Real-Time Fluorescence PCR with the LightCycler", Technical Briefs, pp. 694-696, (May 1999).

Rouet et al., "Field Evaluation of a Rapid Human Immunodeficiency Virus (HIV) Serial Serologic Testing Algorithm for Diagnosis and Differentiation of HIV Type 1 (HIV-1), HIV-2, and Dual HIV-1-HIV-2 Infections in West African Pregnant Women", Journal of Clinical Microbiology, pp. 4147-4153, vol. 42, No. 9 (Sep. 2004).

Visseaux et al., "HIV-2 Group A in France Displayed 2 Clades With Distinct Geographical Origins", Program and Agenda Session P-B1 poster Abstracts, (Feb. 2016).

\* cited by examiner

SEQUENCE LISTING

<160> NUMBER OF SEQ ID NOS: 13

<210> SEQ ID NO 1
<211> LENGTH: 21
<212> TYPE: DNA
<213> ORGANISM: Artificial sequence
<220> FEATURE:
<223> OTHER INFORMATION: PCR primer

<400> SEQUENCE: 1
agcaggtaga gcctgggtgt t                                               21

<210> SEQ ID NO 2
<211> LENGTH: 21
<212> TYPE: DNA
<213> ORGANISM: Artificial sequence
<220> FEATURE:
<223> OTHER INFORMATION: PCR primer

<400> SEQUENCE: 2
tctttaagca agcaagcgtg g                                               21

<210> SEQ ID NO 3
<211> LENGTH: 20
<212> TYPE: DNA
<213> ORGANISM: Artificial sequence
<220> FEATURE:
<223> OTHER INFORMATION: Probe

<400> SEQUENCE: 3
cttggccggy rctgggcaga                                                 20

<210> SEQ ID NO 4
<211> LENGTH: 20
<212> TYPE: DNA
<213> ORGANISM: Artificial sequence
<220> FEATURE:
<223> OTHER INFORMATION: PCR primer

<400> SEQUENCE: 4
gcgcgagaaa ctccgtcttg                                                 20

<210> SEQ ID NO 5
<211> LENGTH: 22

```
<212> TYPE: DNA
<213> ORGANISM: Artificial sequence
<220> FEATURE:
<223> OTHER INFORMATION: PCR primer

<400> SEQUENCE: 5
ttcgctgccc acacaatatg tt                                            22

<210> SEQ ID NO 6
<211> LENGTH: 23
<212> TYPE: DNA
<213> ORGANISM: Artificial sequence
<220> FEATURE:
<223> OTHER INFORMATION: Probe

<400> SEQUENCE: 6
taggttacgg cccggcggaa aga                                           23

<210> SEQ ID NO 7
<211> LENGTH: 21
<212> TYPE: DNA
<213> ORGANISM: Artificial sequence
<220> FEATURE:
<223> OTHER INFORMATION: PCR primer

<400> SEQUENCE: 7
aacacccagg ctctacctgc t                                             21

<210> SEQ ID NO 8
<211> LENGTH: 21
<212> TYPE: DNA
<213> ORGANISM: Artificial sequence
<220> FEATURE:
<223> OTHER INFORMATION: PCR primer

<400> SEQUENCE: 8
ccacgcttgc ttgcttaaag a                                             21

<210> SEQ ID NO 9
<211> LENGTH: 20
<212> TYPE: DNA
<213> ORGANISM: Artificial sequence
<220> FEATURE:
<223> OTHER INFORMATION: Probe

<400> SEQUENCE: 9
tctgcccagy rccggccaag                                               20

<210> SEQ ID NO 10
<211> LENGTH: 20
<212> TYPE: DNA
<213> ORGANISM: Artificial sequence
<220> FEATURE:
<223> OTHER INFORMATION: PCR primer

<400> SEQUENCE: 10
caagacggag tttctcgcgc                                               20

<210> SEQ ID NO 11
<211> LENGTH: 22
<212> TYPE: DNA
<213> ORGANISM: Artificial sequence
<220> FEATURE:
<223> OTHER INFORMATION: PCR primer

<400> SEQUENCE: 11
```

```
aacatattgt gtgggcagcg aa                                              22

<210> SEQ ID NO 12
<211> LENGTH: 22
<212> TYPE: DNA
<213> ORGANISM: Artificial sequence
<220> FEATURE:
<223> OTHER INFORMATION: Probe

<400> SEQUENCE: 12
ctttccgccg ggccgtaacc ta                                              22

<210> SEQ ID NO 13
<211> LENGTH: 9671
<212> TYPE: DNA
<213> ORGANISM: Human immunodeficiency virus type 2

<400> SEQUENCE: 13
ggtcgctctg cggagaggct ggcagattga gccctgggag gttctctcca gcactagcag      60
gtagagcctg ggtgttccct gctagactct caccagcact tggccggtgc tgggcagacg     120
gccccacgct tgcttgctta aaaacctctt aataaagctg ccagttagaa gcaagttaag     180
tgtgtgctcc catctctcct agtcgccgcc tggtcattcg tgttcacct gagtaacaag     240 accctggtct gttaggaccc ttcttgcttt gggaaaccga ggcaggaaaa tccctagcag     300 gttgcgcct gaacagggac ttgaagaaga ctgagaagtc ttggaacacg ctgagtgaa      360 ggcagtaagg gcggcaggaa caaaccacga cggagtgctc ctagaaaggc gcgggccgag     420
gtaccaaagg cagcgtgtgg agcgggagga gaagaggcct ccgggtgaag gtaagtacct     480
acaccaaaaa ctgtagccga agggcttgc tatcctacct ttagacaggt agaagattgt     540
gggagatggg cgcgagaaac tccgtcttga gagggaaaaa agcagatgaa ttagaaagaa     600
tcaggttacg gcccggcgga agaaaaagt acaggctaaa acatattgtg tgggcagcga     660
ataaattgga cagattcgga ttagcagaga gcctgttgga gtcaaaagag ggttgtcaaa     720
aaattcttac agttttagat ccaatggtac cgacaggttc agaaaattta aaaagtcttt     780
ttaatactgt ctgcgtcatt tggtgcatac acgcagaaga gaaagtgaaa gatactgaag     840
gagcaaaaca aatagtgcgg agacatctag tggcagaaac aggaactgca gagaaatgc      900 caagcacaag tagaccaaca gcaccatcta gcgagaaggg aggaaattac ccagtgcaac     960
atgtaggcgg caactacacc catataccgc tgagtccccg aaccctaaat gcctgggtaa    1020
aattagtaga ggaaaaaaag ttcggggcag aagtagtgcc aggatttcag gcactctcag    1080
aaggctgcac gccctatgat atcaaccaaa tgcttaattg tgtgggcgac catcaagcag    1140
ccatgcagat aatcagggag attatcaatg aggaagcagc agaatgggat gtgcaacatc    1200
caataccagg cccccttacca gcgggcagc ttagagagcc aaggggatct gacatagcag    1260
ggacaacaag cacagtagaa gaacagatcc agtggatgtt taggccacaa aatcctgtac    1320
cagtaggaaa catctataga gatggatcc agataggatt gcagaagtgt gtcaggatgt    1380
acaacccgac caacatccta gacataaaac agggaccaaa ggagccgttc caaagctatg    1440
tagatagatt ctacaaaagc ttgagggcag aacaaacaga tccagcagtg aagaattgga    1500
tgacccaaac actgctagta caaatgcca acccagactg taaattagtg ctaaaaggac    1560
tagggatgaa ccctacctta gaagagatgc tgaccgcctg tcaggggta ggtgggccag    1620 gccagaaagc tagattaatg gcagaggccc tgaaagaggt cataggacct gcccctatcc    1680
cattcgcagc agcccagcag agaaaggcat ttaaatgctg gaactgtgga aaggaaggc    1740
```

```
actcggcaag acaatgccga gcacctagaa ggcagggctg ctggaagtgt ggtaagccag   1800
gacacatcat gacaaactgc ccagatagac aaggcaggttt tttaggactg ggcccttggg   1860
gaaagaagcc ccgcaacttc cccgtggccc aagttccgca ggggctgaca ccaacagcac   1920 cccagtgga tccagcagtg gatctactgg agaaatatat gcagcaaggg aaaagacaga   1980
gagagcagag agagagacca tacaaggaag tgacagagga cttactgcac ctcgagcagg   2040
gggagacacc atacagggag ccaccaacag aggacttgct gcacctcaat tctctctttg   2100
gaaaagacca gtagtcacag catacattga gggtcagcca gtagaagtct tgttagacac   2160
aggggctgac gactcaatag tagcaggaat agagttaggg aacaattata gcccaaaaat   2220
agtaggggga ataggggggat tcataaatac caaggaatat aaaaatgtag aaatagaagt   2280
tctaaataaa aaggtacggg ccaccataat gacaggcgac accccaatca acattttttgg  2340 cagaaatatt ctgacagcct taggcatgtc attaaatcta ccagtcgcca agtagagcc   2400 aataaaaata atgctaaagc cagggaaaga tggaccaaaa ctgagacaat ggcccttaac   2460
aaaagaaaaa atagaagcac taaaagaaat ctgtgaaaaa atggaaaaag aaggccagct   2520
agaggaagca cctccaacta atccttataa taccccacca tttgcaatca agaaaaagga   2580
caaaaacaaa tggaggatgc taatagattt cagagaacta aacaaggtaa ctcaagattt   2640
cacagaaatt cagttaggaa ttccacaccc agcagggttg gccaagaaga gaagaattac   2700
tgtactagat gtaggggatg cttactttttc cataccacta catgaggact ttagaccata   2760
tactgcattt actctaccat cagtgaacaa tgcagaacca ggaaaaagat acatatataa   2820
agtcttgcca cagggatgga agggatcacc agcaattttt caacacacaa tgagacaggt   2880
attagaacca ttcagaaaag caaacaagga tgtcattatc attcagtaca tggatgatat   2940
cttaatagct agtgacagga cagatttaga acatgatagg gtagtcctgc agctcaagga   3000
acttctaaat ggcctaggat tttctacccc agatgagaag ttccaaaaag accctccata   3060
ccactggatg ggctatgaac tatggccaac taaatggaag ttgcagaaaa tacagttgcc   3120
ccaaaaagaa atatgacag tcaatgacat ccagaagcta gtgggtgtcc taaattgggc   3180
agcacaactc tacccaggga taaagaccaa acacttatgt aggttaatca gaggaaaaat   3240
gacactcaca gaagaagtac agtggacaga attagcagaa gcagagctag aagaaaacag   3300
aattatccta agccaggaac aagagggaca ctattaccaa gaagaaaag gctagaagc   3360 aacagtccaa aaggatcaag agaatcagtg gacatataaa atacaccagg aagaaaaaat   3420
tctaaaagta ggaaaatatg caaaggtgaa aaacacccat accatgaa tcagattgtt   3480 agcacaggta gttcagaaaa taggaaaaga agcactagtc attttgggggac gaataccaaa   3540 atttcacccta ccagtagaga gagaaatctg ggagcagtgg tgggataact actggcaagt   3600
gacatggatc ccagactggg acttcgtgtc taccccacca ctggtcaggt tagcgtttaa   3660
cctggtaggg gatcctatac caggtgcaga gaccttctac acagatggat cctgcaatag   3720
gcaatcaaaa gaaggaaaag caggatatgt aacagataga gggaaagaca aggtaaagaa   3780
actagagcaa actaccaatc agcaagcaga actagaagcc tttgcgatgg cactaacaga   3840
ctcgggtcca aaagttaata ttatagtaga ctcacagtat gtaatgggga tcagtgcaag   3900
ccaaccaaca gagtcagaaa gtaaaatagt gaaccagatc atagaagaaa tgataaaaaaa  3960 ggaagcaatc tatgttgcat gggtcccagc ccacaaaggc ataggggaa accaggaagt   4020 agatcattta gtgagtcagg gtatcagaca agtgttgttc ctggaaaaaa tagagcccgc   4080
```

```
tcaggaagaa catgaaaaat atcatagcaa tgtaaaagaa ctgtctcata aatttggaat    4140
acccaattta gtggcaaggc aaatagtaaa ctcatgtgcc caatgtcaac agaaagggga    4200
agctatacat gggcaagtaa atgcagaact aggcacttgg caaatggact gcacacattt    4260
agaaggaaag atcattatag tagcagtaca tgttgcaagt ggatttatag aagcagaagt    4320
catcccacag gaatcaggaa gacaaacagc actcttccta ttgaaactgg caagtaggtg    4380
gccaataaca cacttgcata cagataatgg tgccaacttc acttcacagg aggtgaagat    4440
ggtagcatgg tggataggta tagaacaatc ctttggagta ccttacaatc cacagagcca    4500
aggagtagta gaagcaatga atcaccatct aaaaaaccaa ataagtagaa tcagagaaca    4560
ggcaaataca atagaaacaa tagtactaat ggcaattcat tgcatgaatt ttaaaagaag    4620 gggggaata ggggatatga ctccatcaga aagattaatc aatatgatca ccacagaaca    4680
agagatacaa ttcctccaag ccaaaaattc aaaattaaaa gattttcggg tctatttcag    4740
agaaggcaga gatcagttgt ggaaggacc tggggaacta ctgtggaaag gagaaggagc    4800
agtcctagtc aaggtaggaa cagacataaa aataatacca agaaggaaag ccaagatcat    4860
cagagactat ggaggaagac aagagatgga tagtggttcc cacctggagg gtgccaggga    4920
ggatggagaa atggcatagc cttgtcaagt atctaaaata caaaacaaag gatctagaaa    4980
aggtgtgcta tgttccccac cataaggtgg gatgggcatg gtggacttgc agcagggtaa    5040
tattcccatt aaaaggaaac agtcatctag agatacaggc atattggaac ttaacaccag    5100
aaaaaggatg gctctcctct tattcagtaa gaataacttg gtacacagaa aagttctgga    5160
cagatgttac cccagactgt gcagatgtcc taatacatag cacttatttc ccttgcttta    5220
cagcaggtga agtaagaaga gccatcagag gggaaaagtt attgtcctgc tgcaattatc    5280
cccgagctca tagagcccag gtaccgtcac ttcaatttct ggccttagtg gtagtgcaac    5340
aaaatgacag accccagaga gacagtacca ccaggaaaca gcggcgaaga gactatcgga    5400
gaggccttcg cctggctaaa caggacagta gaagccataa acagagaagc agtgaatcac    5460
ctaccccgag aacttatttt ccaggtgtgg cagaggtcct ggagatactg gcatgatgaa    5520
caagggatgt cagaaagtta cacaaagtat agatatttgt gcataataca gaaagcagtg    5580
tacatgcatg ttaggaaagg gtgtacttgc ctggggaggg gacatgggcc aggagggtgg    5640
agaccagggc ctcctcctcc tccccctcca ggtctggtct aatggctgaa gcaccaacag    5700
agctcccccc ggtggatggg accccactga gggagccagg ggatgagtgg ataatagaaa    5760
tcttgagaga aataaaagaa gaagctttaa agcattttga ccctcgcttg ctaattgctc    5820
ttggcaaata tatctatact agacatggag acacccttga aggcgccaga gagctcatta    5880
aagtcctgca acgagccctt ttcacgcact tcagagcagg atgtggccac tcaagaattg    5940
gccagacaag gggaggaaat cctctctcag ctataccgac ccctagaaac atgcaataac    6000
tcatgctatt gtaagcgatg ctgctaccat tgtcagatgt gttttctaaa caaggggctc    6060
gggatatgtt atgaacgaaa gggcagacga agaaggactc caaagaaaac taagactcat    6120
ccgtctccta caccagacaa gtgagtatga tgaatcagct gcttattgcc attttattag    6180
ctagtgcttg cttagtatat tgcacccaat atgtaactgt tttctatggc gtacccacgt    6240
ggaaaaatgc aaccattccc ctcttttgtg caaccagaaa tagggatact tggggaacca    6300
tacagtgctt gcctgacaat gatgattatc aggaaataac tttgaatgta acagaggctt    6360
ttgatgcatg gaataataca gtaacagaac aagcaataga agatgtctgg catctattcg    6420
agacatcaat aaaaccatgt gtcaaactaa caccctttatg tgtagcaatg aaatgcagca    6480
```

```
gcacagagag cagcacaggg aacaacacaa cctcaaagag cacaagcaca accacaacca   6540
cacccacaga ccaggagcaa gagataagtg aggatactcc atgcgcacgc gcagacaact   6600
gctcaggatt gggagaggaa gaaacgatca attgccagtt caatatgaca ggattagaaa   6660
gagataagaa aaaacagtat aatgaaacat ggtactcaaa agatgtggtt tgtgagacaa   6720
ataatagcac aaatcagacc cagtgttaca tgaaccattg caacacatca gtcatcacag   6780
aatcatgtga caagcactat tgggatgcta aaggtttag atactgtgca ccaccgggtt   6840
atgccctatt aagatgtaat gataccaatt attcaggctt tgcacccaac tgttctaaag   6900
tagtagcttc tacatgcacc aggatgatgg aaacgcaaac ttccacatgg tttggcttta   6960
atggcactag agcagagaat agaacatata tctattggca tggcagagat aatagaacta   7020
tcatcagctt aaacaaatat tataatctca gtttgcattg taagaggcca gggaataaga   7080
tagtgaaaca aataatgctt atgtcaggac atgtgtttca ctcccactac cagccgatca   7140
ataaaagacc cagacaagca tggtgctggt tcaaaggcaa atggaaagac gccatgcagg   7200
aggtgaagga aacccttgca aaacatccca ggtatagagg aaccaatgac acaaggaata   7260
ttagctttgc agcgccagga aaaggctcag acccagaagt agcatacatg tggactaact   7320
gcagaggaga gtttctctac tgcaacatga cttggttcct caattggata gagaataaga   7380
cacaccgcaa ttatgcaccg tgccatataa agcaaataat taacacatgg cataaggtag   7440
ggagaaatgt atatttgcct cccagggaag gggagctgtc ctgcaactca acagtaacca   7500
gcataattgc taacattgac tggcaaaaca ataatcagac aaacattacc tttagtgcag   7560
aggtggcaga actatacaga ttggagttgg gagattataa attggtagaa ataacaccaa   7620
ttggcttcgc acctcaaaaa gaaaaaagat actcctctgc tcacgggaga catacaagag   7680
gtgtgttcgt gctagggttc ttgggttttc tcgcaacagc aggttctgca atgggcgcgg   7740
cgtccctgac cgtgtcggct cagtcccgga ctttactggc cgggatagtg cagcaacagc   7800
aacagctgtt ggacgtggtc aagagacaac aagaactgtt gcgactgacc gtctgggaa   7860 cgaaaaacct ccaggcaaga gtcactgcta tagagaagta cctacaggac caggcgcggc   7920
taaattcatg gggatgtgcg tttagacaag tctgccacac tactgtacca tgggttaatg   7980
attccttagc acctgactgg acaaatatga cgtggcagga atgggaaaaa caagtccgct   8040
acctggaggc aaatatcagt aaaagtttag aacaggcaca aattcagcaa gagaaaaata   8100
tgtatgaact acaaaaatta aatagctggg atatttttgg caattggttt gacttaacct   8160
cctgggtcaa gtatattcaa tatggagtgc ttataatagt agcagtaata gctttaagaa   8220
tagtgatata tgtagtacaa atgttaagta ggcttagaaa gggctatagg cctgtttct   8280 cttccccccc cggttatatc caacagatcc atatccacaa gaccggggga cagccagcca   8340
acgaagaaac agaagaagac ggtggaagca acggtggaga cagatactgg ccctggccga   8400
tagcatatat acatttcctg atccgccagc tgattcgcct cttgaccaga ctatacagca   8460
tctgcaggga cttactatcc aggagcttcc tgaccctcca actcatctac cagaatctca   8520
gagactggct gagacttaga acagccttct tgcaatatgg gtgcgagtgg atccaagaag   8580
cattccaggc cgccgcgagg gctacaagag agactcttgc gggcgcgtgc aggggcttgt   8640
ggagggtatt ggaacgaatc gggagggaa tactcgcggt tccaagaagg atcagacagg   8700
gagcagaaat cgccctcctg tgagggacgg cagtatcagc agggagactt tatgaatact   8760
ccatggaagg acccagcagc agaaagggag aaaaatttgt acaggcaaca aaatatggat   8820
```

```
gatgtagatt cagatgatga tgaccaagta agagtttctg tcacaccaaa agtaccacta    8880
agaccaatga cacatagatt ggcaatagat atgtcacatt taataaaaac aaggggggga    8940
ctggaaggga tgttttacag tgaaagaaga cataaaatct taaatatata cttagaaaag    9000
gaagaaggga taattgcaga ttggcagaac tacactcatg ggccaggagt aagataccca    9060
atgttctttg ggtggctatg gaagctagta ccagtagatg tcccacaaga aggggaggac    9120
actgagactc actgcttagt acatccagca caaacaagca agtttgatga cccgcatggg    9180
gagacactag tctgggagtt tgatcccttg ctggcttata gttacgaggc ttttattcgg    9240
tacccagagg aatttgggca caagtcaggc ctgccagagg aagagtggaa ggcgagactg    9300
aaagcaagag gaataccatt tagttaaaga caggaacagc tatacttggt cagggcagga    9360
agtaactaac agaaacagct gagactgcag ggacttccca gaaggggctg taaccaaggg    9420
agggacatgg gaggagctgg tggggaacgc cctcatattc tctgtataaa tatacccgct    9480
agcttgcatt gtacttcggt cgctctgcgg agaggctggc agattgagcc ctgggaggtt    9540
ctctccagca gtagcaggta gagcctgggt gttccctgct agactctcac cagcacttgg    9600
ccggtgctgg gcagacggcc ccacgcttgc ttgcttaaaa acctccttaa taaagctgcc    9660
agttagaagc a                                                        9671
```

IN VITRO METHOD FOR DETECTING AND QUANTIFYING HIV-2 DNA

FILED OF THE INVENTION

The present invention relates to an in vitro method for the detection and quantification of Human Immunodeficiency Virus 2 (HIV-2).

TECHNICAL BACKGROUND

HIV-2 infection, mainly limited to West Africa, is characterized by a slow progression of the disease associated with a slow decrease in the number of $CD4^+$ T lymphocytes, a low rate of sexual or vertical transmission and a viral replication lower than the one of HIV-1.

Furthermore, individuals infected with HIV-2 are naturally resistant to non-nucleoside reverse transcriptase inhibitors (NNRTIs), fusion inhibitors (e.g. Enfuvirtide), and certain protease inhibitors (PIs). The treatment of individuals infected with HIV-2 therefore requires a therapeutic management specific and different from individuals infected with HIV-1.

However, the detection of individual infected by HIV-2 is difficult. Indeed, even in the absence of antiretroviral therapy, a large proportion of these individuals has an undetectable HIV-2 RNA plasma load. Thus, in the French national cohort of HIV-2 (1086 patients in May 2016), 71% of individuals who had never received antiretroviral therapy had viral loads of HIV-2 RNA less than 100 copies/mL. In addition, data from infected individuals in West Africa revealed that in 46.5% of individuals who had never received antiretroviral therapy, HIV-2 RNA was undetectable (<10 copies/mL) and that in 35.8% of individuals, the HIV-2 RNA load was between 10 and 100 copies/mL.

In, this context, the HIV-2 DNA is currently considered as the only detectable alternative marker in individuals whose HIV-2 RNA is undetectable.

This marker is notably useful for confirming the diagnosis of a mono- or co-infection with HIV-1 in cases of high cross serological reactivity. In addition, the detection of HIV-2 DNA is essential for early diagnosis in children born from HIV-2 HIV-positive mothers. Finally, this marker may be useful for pathophysiological studies of HIV-2 reservoirs.

Several techniques for quantifying HIV-2 DNA are part of the state of the art, such as the one described in Damond et al. (2001) *J. Clin. Microbiol.* 39: 4264-4268 in which the authors perform a real-time polymerase chain reaction (PCR) to amplify the Gag region of the viral genome.

However, current techniques of HIV-2 DNA present difficulties for quantifying HIV-2 DNA of group B. In addition, they suffer from a lack of sensitivity and are not always able to detect HIV-2 DNA in samples from infected individuals.

Moreover, no quantification test for HIV-2 DNA is currently commercially available.

Thus, the object of the invention is to provide a method for detecting and quantifying HIV-2 DNA by overcoming these difficulties, in particular by improving the reproducibility, sensitivity and/or specificity of the methods of the state of the art, in particular for the two endemic groups A and B of HIV-2.

SUMMARY OF THE INVENTION

The present invention arises from the unexpected demonstration, by the inventors, that a real-time PCR performed with a set of primers of sequences SEQ ID NO: 1 and 2 and a probe of sequence SEQ ID NO: 3, and a set of primers of sequences SEQ ID NO: 4 and 5 and a probe of sequence SEQ ID NO: 6, enables to reproducibly detect and quantify HIV-2 DNA of types A and B with a specificity of 100%, a limit of detection at 3 copies/PCR and a limit of quantification at 6 copies/PCR.

The present invention thus relates to a method for detecting or quantifying deoxyribonucleic acid (DNA) of human immunodeficiency virus 2 (HIV-2) in a sample containing DNA comprising:

a) performing a real-time polymerase chain reaction (PCR) on the sample, or a fraction thereof comprising DNA, with at least two sets of primers and probe each respectively comprising two primers and one labelled probe for the detection or quantification of HIV-2 DNA, at least one of the sets is selected from the group consisting of:

a set comprising a primer comprising or consisting of a sequence SEQ ID NO: 1 or a sequence having at least 90% identity to SEQ ID NO: 1, a primer comprising or consisting of a sequence SEQ ID NO: 2 or a sequence having 90% identity to SEQ ID NO: 2 or the complementary of these sequences, and a labelled probe comprising or consisting of a sequence SEQ ID NO: 3, or a sequence having at least 90% identity to SEQ ID NO: 3 or the complementary of these sequences, and a set comprising a primer comprising or consisting of a sequence SEQ ID NO: 4 or a sequence having at least 90% identity to SEQ ID NO: 4, a primer comprising or consisting of a sequence SEQ ID NO: 5 or a sequence having 90% identity to SEQ ID NO: 5 or the complementary of these sequences, and a labelled probe comprising or consisting of a sequence SEQ ID NO: 6, or a sequence having at least 90% identity to SEQ ID NO: 6 or the complementary of these sequences, and b) determining therefrom the presence or absence and/or the quantity of HIV-2 DNA in the biological sample.

In an embodiment of the invention, in the method for detecting or quantifying HIV-2 DNA as defined above, step a) of performing a real-time polymerase chain reaction (PCR) on the sample, or a fraction thereof comprising DNA, is performed with:

(i) at least 4 primers respectively comprising or consisting of:

a sequence SEQ ID NO: 1 or a sequence having at least 90% identity to SEQ ID NO: 1 or the complementary of these sequences, and a sequence SEQ ID NO: 2 or a sequence having 90% identity to SEQ ID NO: 2 or the complementary of these sequences, and a sequence SEQ ID NO: 4 or a sequence having 90% identity to SEQ ID NO: 4 or the complementary of these sequences, and a sequence SEQ ID NO: 5 or a sequence having 90% identity to SEQ ID NO: 5 or the complementary of these sequences, and (ii) at least 2 labelled probes respectively comprising or consisting of:

a sequence SEQ ID NO: 3, a sequence complementary to SEQ ID NO: 3, or a sequence having at least 90% identity to SEQ ID NO: 3 or the complementary thereof, and a sequence SEQ ID NO: 6, a sequence complementary to SEQ ID NO: 6, or a sequence having at least 90% identity to SEQ ID NO: 6 or the complementary thereof.

In a particular embodiment of the method as defined above, at least one DNA virus or at least one DNA molecule having essentially no sequence similarity with the genomic sequence of HIV-2 is added to the sample or the fraction thereof, as well as the primers and probe necessary for its amplification and detection by real-time PCR, as an internal control of extraction and/or inhibition.

In another embodiment of the invention, the method for detecting or quantifying HIV-2 DNA as defined above further comprises determining or quantifying HIV-1 nucleic acids in a sample or a fraction thereof.

The present invention also relates to a kit or a mix for detecting or quantifying HIV-2 DNA, comprising:

a) at least two sets of primers and probe each respectively comprising two primers and one probe for the detection or quantification of HIV-2 DNA, preferably the primers and probe being each present in a concentration comprised between 300 and 500 nM, and at least one of the sets is selected from the group consisting of:

- a set comprising a primer comprising or consisting of a sequence SEQ ID NO: 1 or a sequence having at least 90% identity to SEQ ID NO: 1, a primer comprising or consisting of a sequence SEQ ID NO: 2 or a sequence having 90% identity to SEQ ID NO: 2 or the complementary of these sequences, and a labelled probe, in particular with 6-carboxyfluorescein (FAM) at its 5'end and with Black Hole Quencher-1 (BHQ1) at its 3' end, comprising or consisting of a sequence SEQ ID NO: 3, or a sequence having at least 90% identity to SEQ ID NO: 3 or the complementary of these sequences, et
- a set comprising a primer comprising or consisting of a sequence SEQ ID NO: 4 or a sequence having at least 90% identity with SEQ ID NO: 4, a primer comprising or consisting of a sequence SEQ ID NO: 5 or a sequence having 90% identity to SEQ ID NO: 5 or the complementary of these primers, and a labelled probe, in particular with 6-carboxyfluorescein (FAM) at its 5'end and with Black Hole Quencher-1 (BHQ1) at its 3' end, comprising or consisting of a sequence SEQ ID NO: 6, or a sequence having at least 90% identity to SEQ ID NO: 6 or the complementary of these sequences, et b) at least one DNA virus or at least one DNA molecule having essentially no sequence similarity with the genomic sequence of HIV-2, as well as the primers and probe necessary for its amplification and detection by real-time PCR, as an internal control of extraction and/or inhibition, and c) optionally additional reagents for performing a PCR.

In another particular embodiment of the invention, the kit or the mix as defined above comprises:

a1) at least 4 primers, preferably at a concentration comprised between 300 and 500 nM, respectively comprising or consisting of:

- a sequence SEQ ID NO: 1 or a sequence having at least 90% identity to SEQ ID NO: 1 or the complementary of these sequences, and
- a sequence SEQ ID NO: 2 or a sequence having 90% identity to SEQ ID NO: 2 or the complementary of these sequences, and
- a sequence SEQ ID NO: 4 or a sequence having 90% identity to SEQ ID NO: 4 or the complementary of these sequences, and
- a sequence SEQ ID NO: 5 or a sequence having 90% identity to SEQ ID NO: 5 or the complementary of these sequences, and a2) at least 2 labelled probes, in particular with 6-carboxyfluorescein (FAM) at their 5'end and with Black Hole Quencher-1 (BHQ1) at their 3' end, preferably at a concentration comprised between 300 and 500 nM, respectively comprising or consisting of:

- a sequence SEQ ID NO: 3, a sequence complementary to SEQ ID NO: 3, or a sequence having at least 90% identity to SEQ ID NO: 3 or the complementary thereof, and
- a sequence SEQ ID NO: 6, a sequence complementary to SEQ ID NO: 6, or a sequence having at least 90% identity to SEQ ID NO: 6 or the complementary thereof.

In an embodiment of the invention, the kit or the mix as defined above further comprises primers and at least one labelled probe for detecting or quantifying HIV-1 nucleic acids.

The present invention also relates to the use of the kit or the mix as defined above, for detecting or quantifying HIV-2 nucleic acids of a sample containing DNA.

The present invention also relates to a method, in particular an in vitro method, for diagnosing HIV-2 infection, or determining HIV-2 viral load, in an individual, comprising the steps of:

(a) performing the method for detecting or quantifying HIV-2 DNA in a biological sample taken from the individual as defined above;
(b) determining therefrom whether the individual is infected by HIV-2 or the HIV-2 viral load of the individual.

The present invention also relates to a method, in particular an in vitro method, for determining whether an individual is liable to benefit from a treatment of HIV-2 infection or an adjustment of the treatment, comprising performing the method for diagnosing HIV-2 infection, or determining HIV-2 viral load, as defined above.

The present invention also relates to a method, in particular an in vitro method, for monitoring the HIV-2 viral load of an individual treated for HIV-2 infection, comprising performing the method for diagnosing HIV-2 infection, or determining HIV-2 viral load as defined above.

The present invention also relates to Nucleoside reverse transcriptase inhibitors (NRTIs), Protease inhibitors (PIs) and/or Integrase inhibitors for use in the prevention or treatment of HIV-2 infection in an individual, wherein the individual has been determined to be liable to benefit from a treatment of HIV-2 infection by the method as defined above.

DETAILED DESCRIPTION OF THE INVENTION

HIV-2 DNA

The human immunodeficiency virus 2 (HIV-2), for which the infection can lead to acquired immunodeficiency syndrome (AIDS) is well known to one of skill in the art. HIV-2 is a member of the genus Lentivirus, which belongs to the family Retroviridae. Its replication cycle involves the entry of HIV-2 single-stranded RNA into a cell, reverse transcription to give a single-stranded DNA and then a double-stranded DNA which is integrated into the genome of the host cell. The HIV-2 according to the invention may be of any group, in particular of group A, B or of non-endemic groups, in particular C, D. E or H. Advantageously, the method according to the invention detects or quantifies the HIV-2 DNA of group A or B in a sample with a specificity of the order of 100%.

As intended herein, the term "VIH-2 DNA" refers to the DNA encoding the genome of HIV-2 in a whole or in part. The HIV-2 DNA to be detected or quantified according to the invention can thus be in particular a single-stranded DNA, especially a sense or antisense single-stranded DNA, or a double-stranded DNA.

Real-Time PCR

Real-time Polymerase Chain Reaction (PCR) is well-known to one of skill in the art and is also known as quantitative PCR (qPCR).

One of skill in the in art can readily determine from a real-time PCR whether VIH-2 DNA is present, i.e. detect and/or quantify the VIH-2 DNA. Typically, in real-time PCR a signal, generally a fluorescent signal, which intensity is a consequence of the accumulation of amplified DNA is measured by the thermal cycler which runs the PCR. If, in the course of the PCR, the intensity of the measured signal, in particular the fluorescent signal, is higher than a signal threshold, generally background signal intensity, it is deduced that amplification has occurred, i.e. that HIV-2 DNA is present in the biological sample. Conversely, if no signal intensity higher than background signal intensity is measured in the course of PCR, it is deduced that no DNA molecule is present in the biological sample or that the quantity of DNA is below the detection level. Besides, the cycle of the PCR at which a signal intensity higher than the background signal intensity is measured, is named the threshold cycle ($C_T$). It is well-known to one of skill in the art that $C_T$ values are proportional to the $\log_{10}$ of the starting amounts of DNA in the sample submitted to the real-time PCR. Accordingly, the quantity of DNA present, i.e. the DNA load of the biological sample, can be readily determined, if necessary, by reference to a standard curve.

Numerous real-time PCR techniques, generally differing in the signal generation system and the labelled probes used, can be used according to the invention, such as the so-called Taqman or Molecular Beacons assays. Preferably, the PCR according to the invention is of the Taqman type. Taqman type real-time PCR is well-known to one of skill in the art and has been originally described in 1991 by Holland et al. (1991) *Proc. Natl. Acad. Sci. USA* 88:7276-7280.

Briefly, TaqMan probes consist of a fluorophore covalently attached to the 5'-end of an oligonucleotide probe and another type of fluorophore named quencher at the 3'-end. The probe is such that the quencher molecule quenches the fluorescence emitted by the fluorophore when excited by a thermocycler's light source, this phenomenon being known as fluorescence resonance energy transfer or FRET. Thus, as long as the fluorophore and the quencher are in proximity, i.e. are attached to the probe, quenching inhibits any fluorescence signals. Besides. TaqMan probes are designed such that they anneal to a target within amplified DNA region. As the thermostable polymerase used for performing PCR extends the primer and synthesizes the nascent strand, its 5' to 3' exonuclease activity degrades the probe that has annealed to the template. Degradation of the probe releases the fluorophore from it and breaks the close proximity to the quencher, thus relieving the quenching effect and allowing fluorescence of the fluorophore. Hence, fluorescence detected in the quantitative PCR thermal cycler is directly proportional to the fluorophore released and the amount of DNA template present in the PCR.

Preferably, the real-time PCR according to the invention comprises the following thermocycling conditions:
2 min at 50° C. followed by
10 min at 95° C., followed by
50 cycles of 95° C. for 5 sec and 60° C. for 1 min.

Advantageously, the above-defined thermocycling conditions are compatible, or identical, to those used for the detection and/or quantification of HIV-1 DNA, in particular using the GENERIC HIV DNA CELL assay of Biocentric (Grasse, France). Accordingly, the method for detecting or quantifying VIH-2 DNA in a sample containing DNA according to the invention can be used on the same thermocycler, with the same software program and even, if necessary, in the same amplification plate, as samples intended for HIV-1 DNA detection or quantification, or the same samples.

Primers and Probes

As intended herein a primer is an oligonucleotide, preferably a DNA oligonucleotide, useful to prime replication by a DNA polymerase, in particular a thermostable DNA polymerase. Preferably, primers according to the invention comprise no more than 50 nucleotides, more preferably no more than 40 nucleotides, and most preferably no more than 30 nucleotides.

As intended herein a probe is an oligonucleotide, preferably a DNA oligonucleotide, which can anneal to DNA molecules amplified, i.e. to amplimers, as part of the real-time PCR according to the invention. Preferably, probes according to the invention comprise no more than 50 nucleotides, more preferably no more than 40 nucleotides, and most preferably no more than 30 nucleotides. The labelled probe is such that a detectable signal, preferably fluorescence, is emitted and increases in intensity as a consequence of the accumulation of amplified DNA molecules. More preferably the probes according to the invention are labelled, in particular covalently labelled, by a first fluorophore and by a second quencher-type fluorophore, the fluorophore-quencher pair being such that the quencher quenches fluorescence emission by the fluorophore. In this frame, it is preferred that the fluorophore is attached at or near the 5' end of the probe and that the quencher is attached at or near the 3' end of the probe. Numerous suitable fluorophore-quencher pairs according to the invention can be devised by one of skill in the art. By way of example, the fluorophore-quencher pairs 6-carboxyfluorescein (FAM)-carboxytetramethylrhodamine (TAMRA) and 6-carboxyfluorescein (FAM)-Black Hole Quencher-1 (BHQ1) are suitable for the labelled probes according to the invention. A particularly preferred fluorophore-quencher pair according to the invention is 6-carboxyfluorescein (FAM)-Black Hole Quencher-1 (BHQ1). Besides it is also preferred that the 2 labelled probes according to the invention are labelled by a same fluorophore-quencher pair. Thus, it is particularly preferred that the 2 labelled probes are labelled with 6-carboxyfluorescein (FAM) at their 5' end and with Black Hole Quencher-1 (BHQ1) at their 3' end.

As intended herein, where a primer or a probe according to the invention is said to "comprise" a particular sequence, the primer or the probe may also comprise additional sequences extending from the 5' end and/or 3' end of the particular sequence. In contrast, where a primer or a probe according to the invention "consists of" a particular sequence, the primer or the probe does not comprise supplementary sequences in addition to the particular sequence.

Preferably, the at least 4 primers according to the invention respectively consist of sequences SEQ ID NO: 1, SEQ ID NO: 2. SEQ ID NO: 4 and SEQ ID NO: 5, and the 2 labelled probes according to the invention respectively consist of sequences SEQ ID NO: 3 and SEQ ID NO: 6.

As intended herein, a "sequence having at least 90% identity to SEQ ID NO: X", in particular differs from SEQ ID NO: X by the insertion, the suppression or the substitution of at least one nucleotide. Besides, the percentage of identity between two nucleotide sequences is defined herein as the number of positions for which the bases are identical when the two sequences are optimally aligned, divided by the total number of bases of the longest of the two sequences. Two sequences are said to be optimally aligned when the percentage of identity is maximal. Besides, according to the usual practice of one of skill in the art, it is possible to add a limited number of gaps in order to obtain an optimal alignment between the two sequences.

Preferably, a sequence according to the invention having at least 90% identity to SEQ ID NO: 1, 2, 3, 4, 5 or 6 has respectively at least 95%, more preferably at least 98% identity with SEQ ID NO: 1, 2, 3, 4, 5 or 6.

The primers according to the invention comprising sequences SEQ ID NO: 1 and SEQ ID NO: 2 or sequences having at least 90% identity to SEQ ID NO: 1 and SEQ ID NO: 2 and the probe comprising or consisting of sequence SEQ ID NO: 3, a sequence complementary to SEQ ID NO: 3, or a sequence having at least 90% identity to SEQ ID NO: 3 or the complementary thereof, are useful to detect a portion of the LTR region of HIV-2 genome.

The primers according to the invention comprising sequences SEQ ID NO: 4 and SEQ ID NO: 5 or sequences having at least 90% identity to SEQ ID NO: 4 and SEQ ID NO: 5 and the probe comprising or consisting of sequence SEQ ID NO: 6, a sequence complementary to SEQ ID NO: 6, or a sequence having at least 90% identity to SEQ ID NO: 6 or the complementary thereof, are useful to detect a portion of the Gag region of HIV-2 genome.

As will be clear to one of skill in the art and by way of example, the sequence complementary to a sequence:

```
                                    (SEQ ID NO: 1)
5'-AGCAGGTAGAGCCTGGGTGTT-3'
is (SEQ ID NO: 7)
5'-AACACCCAGGCTCTACCTGCT-3';

(SEQ ID NO: 2)
5'-TCTTTAAGCAAGCAAGCGTGG-3'
is (SEQ ID NO: 8)
5'-CCACGCTTGCTTGCTTAAAGA-3';

(SEQ ID NO: 3)
5-CTTGGCCGGYRCTGGGCAGA-3'
is (SEQ ID NO: 9)
5'-TCTGCCCAGYRCCGGCCAAG-3';

(SEQ ID NO: 4)
5'-GCGCGAGAAACTCCGTCTTG-3'
is (SEQ ID NO: 10)
5'-CAAGACGGAGTTTCTCGCGC-3';

(SEQ ID NO: 5)
5'-TTCGCTGCCCACACAATATGTT-3'
is
```

```
                                    (SEQ ID NO: 11)
5'-AACATATTGTGTGGGCAGCGAA-3';

(SEQ ID NO: 6)
5'-TAGGTTACGGCCCGGCGGAAAGA-3'
is (SEQ ID NO: 12)
5'-CTTTCCGCCGGGCCGTAACCTA-3';
```

Besides, as will also be clear to one of skill in the art SEQ ID NO: 3 (CTTGGCCGGYRCTGGGCAGA) is a so-called degenerated sequence wherein Y represents C and T. and R represents A and G.

Preferably, primers and probes according to the invention, are present in a concentration comprised between 300 and 500 nM each. Preferably also, primers and probes are all present at the same concentration. Most preferably, the primers and probes are present at a concentration of 400 nM.

Advantageously, the use of primers and probes according to the invention in real-time PCR (i) provides for the specific detection and quantification of HIV-2 DNA over HIV-1 nucleic acids. (ii) lowers the detection and quantification limit of the prior art assays, and (iii) provides for an improved detection and quantification of subtype B HIV-2 DNA.

Internal Control

In the present invention, the internal control of extraction and/or inhibition notably enables to validate the entire analytical process by real-time PCR, from extraction to amplification, without competition between HIV-2 DNA and internal control, including for weak values.

As intended herein the term "internal control of extraction and/or inhibition" refers to an exogenous DNA virus or nucleic acid molecule having essentially no sequence similarity with the human genome or with pathogens affecting the humans.

Preferably, the internal control of extraction and/or inhibition according to the invention is a DNA molecule.

Preferably, the internal control according to the invention as well as the primers and probe necessary for its amplification and detection by real-time PCR are added before the extraction.

Preferably, the internal control of extraction and/or inhibition according to the invention is labeled with a fluorochrome. More preferably, the internal control of extraction and/or inhibition according to the invention is marked by the fluorochrome Yellow Dye ref. DICD-YD-L100.

Sample Containing DNA

In the present invention a "sample containing DNA" relates to any sample, in particular solid, fluid or liquid, liable to contain HIV-2 DNA. The sample containing the DNA according to the invention may in particular be a biological sample or a sample, in particular of experimental type, containing cells or fractions of cells infected in vitro by HIV-2.

Preferably, the biological sample according to the invention is derived from a sample taken from an individual, in particular a human individual, and may notably be a whole blood sample, a plasma sample, a serum sample, a seminal sample, a sample of peripheral blood mononuclear cells (PBMC), or fractions thereof, or a sample of leukocytes, or fractions thereof.

As will be clear to one of skill in the art, the sample containing DNA according to the invention may have been treated, in particular after being taken from the individual, before being subjected to a real-time PCR according to the invention. Such treatments include centrifugation, treatment with an anticoagulant such as EDTA, or concentration, purification or extraction of DNA. Thus, for example, a biological sample according to the invention may be a DNA solution of a sample, such as a whole blood sample, taken from a human individual.

Kit and Mix

As intended herein in a "kit" according to the invention, one or more of the components of the kit may be packaged or compartmented separately from the rest of the components.

As intended herein in a "mix" according to the invention, all the components of the mix are in a single compartment. Preferably, the mix according to the invention is a PCR mix.

Additional reagents to the primers and probes according to the invention can be easily devised by one of skill in the art and notably encompass a thermostable DNA polymerase, a reverse transcriptase, dNTPs, salts, in particular $Mn^{2+}$ and $Mg^{2+}$ salts, and buffers.

Treatment of an HIV-2 Infection

In the present invention, a "treatment of HIV-2 infection" refers to any treatment for preventing or treating an HIV-2 infection, in particular by reducing the viral load of HIV-2 or rendering it undetectable.

Preferably, the treatment of an HIV-2 infection according to the invention is selected from the group consisting of antiretroviral therapy (ART), in particular using a nucleoside reverse transcriptase inhibitor (NRTI), a protease inhibitor (PI) and/or an integrase inhibitor, an immunomodulator, a molecule capable of acting at the level of the immune control points, a monoclonal antibody, an anti-latency molecule having an epigenetic mechanism of action and a vaccine.

The present invention will be further described by the following non-limiting figures and example.

DESCRIPTION OF THE FIGURES

FIGS. 2 and 3
FIGS. 2A-2B represent $log_{10}$ of the number of HIV-2 DNA copies obtained by automatic extraction from $10^6$ PBMCs (FIG. 2A) or leukocytes (FIG. 2B) (vertical axis) as a function of $log_{10}$ of the number of HIV-2 DNA copies obtained by manual extraction from $10^6$ PBMCs (FIG. 2A) or leukocytes (FIG. 2B) (horizontal axis). PBMCs being from cellular pellets (FIG. 2A) and leukocytes from whole blood (FIG. 2B). The correlation coefficient (r) and the significance threshold (p) are represented.

EXAMPLE

Materials and Methods
Biological Samples According to the Invention
Frozen aliquots of peripheral blood mononuclear cells (PBMCs) from 63 HIV-2 infected patients included in the French National HIV-2 Cohort (ANRS CO5) were selected according to viral genotype and plasma HIV-2 RNA load, determined as described in Avettand-Fenoel et al. (2014) *J. Clin. Microbiol.* 52: 3017-3022. Written informed consent was obtained from all patients at the time of inclusion in the cohort. Among the 63 patients, 71% (n=45) were treated by antiretroviral therapy, and concerning the viral group, determined as described in Charpentier et al. (2014) *AIDS Lond Engl* 28: 1161-1169, 35 of them presented a group A virus (71% treated) and 28 presented a group B virus (71% treated). The selected samples had the following characteristics: HIV-2 RNA load<40 copies/ml (n=28:15 group A and 13 group B), 40 to 500 copies/ml (n=18; 10 group A and 8 group B), 500 to 5.000 copies/ml (n=9; 4 group A and 5 group B) and 5,000 to 50,000 copies/ml (n=8; 6 group A and 2 group B). These samples were used to evaluate the clinical performance of the assay. Eleven whole blood samples from HIV-2 infected patients (6 group A and 5 group B) were also used to evaluate performance of the method on whole blood.

Blood samples from 30 HIV-negative subjects, 40 HIV-1 group M-positive patients and 10 HIV-1 group O patients were tested to evaluate the specificity of the method according to the invention.
Detection and Quantification of HIV-2 DNA According to the Invention
Several extraction methods were used for whole blood and cell pellets, depending on the laboratory out of three (A, B and C) involved in the study. For whole blood, total DNA was extracted from 200 µl using the NucleoSpin® Blood Kit (Macherey-Nagel, Düren, Germany) in labs A and B and the QIAsymphony DSP DNA mini kit (Qiagen, Courtaboeuf, France) in lab C. For cell pellets, the QIAamp DNA mini kit and the QIAsymphony DSP DNA mini kit were used for total DNA extraction from 3 to 5 million cells in labs A and C, respectively.

To normalize the HIV-2 DNA quantification, the amount of total DNA in extracts was determined by spectrophotometry (Nanodrop, Thermo Scientific, Wilmington. N.C. USA) (labs A and B) or quantification of the albumin gene (lab C) using the LightCycler® FastStart DNA Master Hydroprobe kit (Roche. Mannheim. Germany) and serial dilutions of Human Genomic DNA (Roche) as standard (Laurendeau et al. (1999) *Clin. Chem.* 45: 982-986: Dehee (2001) *J. Med. Viol.* 65: 543-552).

The quantification method according to the invention is based in particular on a triplex TaqMan PCR approach targeting the conserved consensus regions in the long terminal repeat (LTR) and the gag gene. It includes an internal control (yellow dye universal DNA extraction and inhibition control. Diagenode, Liege, Belgium) added before extraction.

The forward and reverse primers for the LTR region were 5'-AGCAGGTAGAGCCTGGGTGTT-3' (SEQ ID NO: 1)

and 5'-TCTTTAAGCAAGCAAGCGTGG-3' (SEQ ID NO: 2) respectively (Rouet et al. *J. Clin. Microbiol.* 42: 4147-53), with an internal probe 5'-FAM-CTTGGCCG-GYRCTGGGCAGA-BHQ1-3'. (SEQ ID NO: 3) where FAM means carboxyfluorescein, and BHQ1 means black hole quencher 1.

The forward and reverse primers for the gag region were 5'-GCGCGAGAAACTCCGTCTTG-3' (SEQ ID NO: 4) and 5'-TTCGCTGCCCACACAATATGTT-3' (SEQ ID NO: 5), respectively, with an internal probe 5'-FAM-TAGGT-TACGGCCCGGCGGAAAGA-BHQ1-3' (SEQ ID NO: 6) (Damond et al. (2005) *J. Clin. Microbiol.* 43: 4234-6).

TABLE 1

Primers and probes used for PCR analysis

|  | LTR | Gag |
|---|---|---|
| Forward primers | 5'-AGCAGGTAGAGCCTGGG TGTT-3' (SEQ ID NO: 1) | 5'-GCGCGAGAAACTCCGTC TTG-3' (SEQ ID NO: 4) |
| Reverse primers | 5'-TCTTTAAGCAAGCAAGC GTGG-3' (SEQ ID NO: 2) | 5'-TTCGCTGCCCACACAAT ATGTT-3' (SEQ ID NO: 5) |
| Probe | 5'-CTTGGCCGGYRCTGGGC AGA-3' (SEQ ID NO: 3) | 5'-TAGGTTACGGCCCGGCG GAAAGA-3' (SEQ ID NO: 6) |

The reaction mix consists of a 50-μl volume containing the DNA extract (20 μl), primers and probes for HIV-2 (400 nM each), primers and probe for the internal control (1 μl), and IX PCR buffer (2× qPCR MasterMix Plus; Eurogentec, Seraing. Belgium).

The thermocycling conditions are as follows: 2 min at 50° C. and 10 min at 95° C., followed by 50 cycles of: 95° C. for 15 s and 60° C. for 1 min. Amplification and data acquisition were carried out with the CFX96 system (Bio-rad, Hercules, Calif. USA) (Lab A) and TaqMan ABI 7900 and 7500 real-time PCR system (Applied Biosystems, Courtaboeuf, France) (Labs B and C, respectively). The $\log_{10}$ number of targets initially present is proportional to the cycle threshold ($C_T$) and was determined from the external standard curve.

DNA from HIV-2 (NIH-Z strain) infected cells (Advanced Biotechnologies Inc, Eldersburg, Md. USA) is used as the external standard. This standard, evaluated at 131.300 copies/μl using a previously described assay (Damond et al. (2005) *J. Clin. Microbiol.* 43: 4234-4236), was first diluted in 200 ng/μl human genomic DNA (Promega, Madison, Wis., USA) to a theoretical concentration of 60,000 copies/20 μl, followed by serial 1/10 dilutions in 25 ng/μl of human genomic DNA to concentrations from 6,000 copies/20 μl down to a final dilution of 2 copies/20 μl.

HIV-2 DNA levels were first reported as HIV-2 DNA copies/PCR. The number of copies of HIV-2 DNA/μg total DNA was then calculated using the extract concentration and the final results were reported as the number of copies/$10^6$ cells. The formula used to convert these results is: HIV-2 DNA (copies/μg total DNA)×1,000,000/150,000=HIV-2 DNA (copies/$10^6$ cells) (Avettand-Fénoël et al. (2009) *J. Med. Virol.* 81: 217-223: Dib et al. (1996) Nature 380: 152-154).

Determination of the Analytical Performance of the HIV-2 DNA Detection and Quantification Method According to the Invention Specificity was determined by testing blood samples from HIV-negative subjects (10 per lab), HIV-1 group M-positive patients (lab A) and HIV-1 group O patients (lab B).

Linearity was assessed in the three labs using serial dilutions of the external standard at 6,000, 600, 60, and 6 copies/20 μl (22 PCRs).

Analytical sensitivity was determined by testing dilutions of the external standard to 10, 6, 4, 3, and 2 copies/20 μl (20 replicates each) (lab A and lab B).

Within-PCR reproducibility was determined by testing the external standard at dilutions of 6000, 600, 60, and 6 copies/20 μl (10 replicates for each dilution) (lab B).

To determine between-PCR reproducibility, an HIV-2-positive control was prepared by dilution of a DNA extract from cell cultures of an HIV-2 group A isolate (GenBank accession number M15390, SEQ ID NO: 13) and quantified at 2.13 $\log_{10}$ copies/20 μl by a previously described assay (Damond et al. (2005) J. Clin. Microbiol. 43: 4234-4236). This solution was tested in the three laboratories in separate PCRs (n=24).

Manual and automated extractions were compared using blood cell pellets and whole blood: 15 PBMCs pellets (8 group A and 7 group B) and 11 whole blood samples (6 group A and 5 group B) were extracted and quantified in parallel in labs A (manual) and C (automated).

Statistical Analysis

Comparisons between groups were performed with the Mann-Whitney test. Pearson's correlation coefficients were calculated to estimate the relationship between the $C_T$ values and $\log_{10}$ of the number of HIV-2 DNA copies/PCR, the relationship between the HIV-2 DNA and HIV-2 RNA loads, and to compare manual versus automated extractions. ANOVA was performed to evaluate the HIV-2 DNA quantification values according to HIV-2 RNA quantification values.

Results

Analytical Performance of the Detection and Quantification Method According to the Invention The 50 HIV-1 positive and 30 HIV-negative DNA samples were negative in the assay, giving a specificity of 100%.

Figure 1:
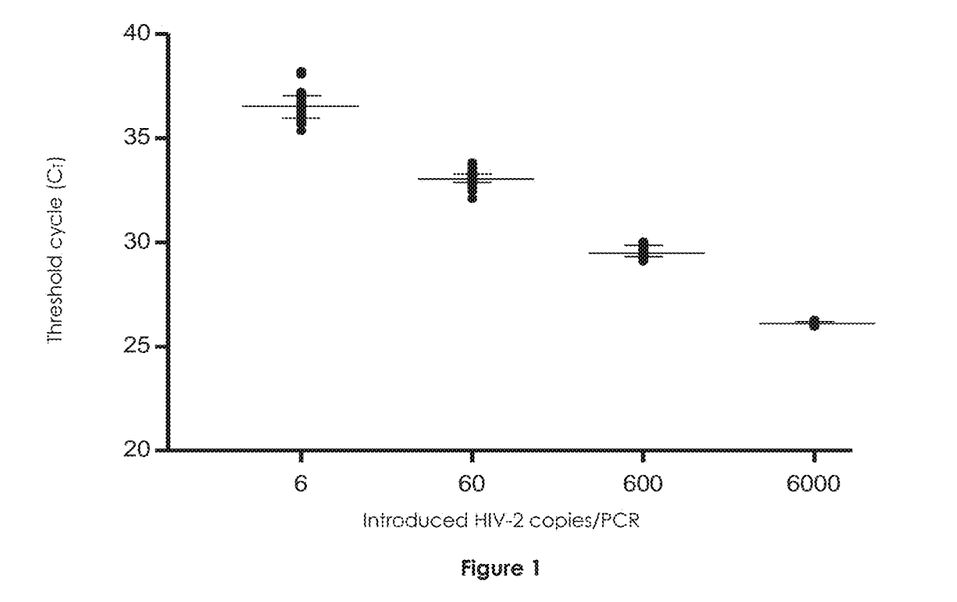
FIG. 1
FIG. 1 represents the standard curve of the threshold cycle ($C_T$) (vertical axis) determined by performing a real-time PCR according to the invention as a function of the number of HIV-2 DNA copies introduced (horizontal axis, logarithmic scale). Median values and interquartiles ranges at 25% and 75% of $C_T$ are shown.

The standard curve shows strong linearity between the $C_T$ values and $\log_{10}$ of the number of HIV-2 DNA copies/PCR, with a limit of quantification of six copies/PCR (FIG. 1). The median correlation coefficient is 0.997 (range, 0.982 to 1), and the median slope is −3.45 (range, −3.11 to −3.64).

The analytical sensitivity of the assay is 100% at 4 copies/PCR, 95% at 3 copies/PCR, and 85% at 2 copies/PCR.

Within-PCR reproducibility was evaluated using the external standard with theoretical concentrations of 6.000, 600, 60, and 6 copies/PCR ($\log_{10}$ of the number of copies/PCR respectively 3.78, 2.78, 1.78, and 0.78). The inventors obtained a mean of 3.80 in $\log_{10}$ copies/PCR for the expected value of 3.78 in $\log_{10}$ copies/PCR with a within-PCR coefficient of variation (CV) of 1.03% and mean values of 2.79, 1.83, and 0.85 in $\log_{10}$ copies/PCR respectively for the expected concentrations of 2.78, 1.78, and 0.78 in $\log_{10}$ copies/PCR, and within-PCR CVs of 1.60%, 3.43%, and 27.02%, respectively.

The positive control was determined to be 2.19 in $\log_{10}$ copies/PCR for the between-PCR assays performed in the three laboratories, with a CV of 5.10%.

Manual and automated extractions were compared using samples extracted and quantified in parallel in labs A and C, respectively. As such, the median values of HIV-2 DNA obtained from the 15 cell pellets were 2.34 in $\log_{10}$ copies/

Figure 2:
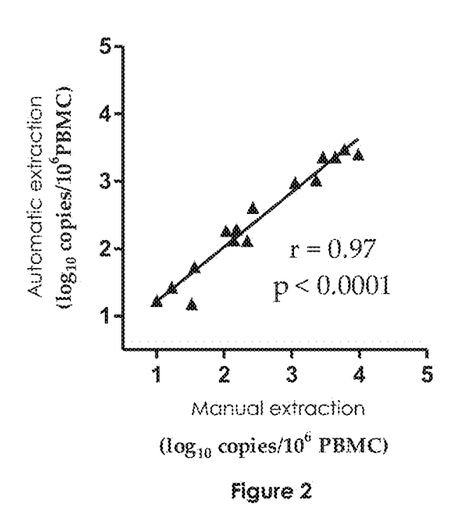
Figure 3:
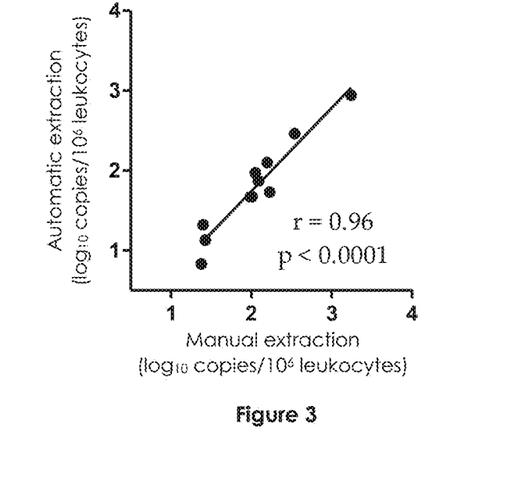

10$^6$ PBMC with manual extraction and 2.29 in log$_{10}$ copies/10$^6$ PBMC with automated extraction, with a median of differences of 0.22 in log$_{10}$ and a correlation coefficient of 0.97 (IC 95%=[0.92; 0.99], p<0.0001). Median values obtained from the 11 whole blood samples were 2.05 in log$_{10}$ copies/10$^6$ leukocytes with manual extraction and 1.73 in log$_{10}$ copies/10$^6$ leukocytes with automated extraction, with a median difference of 0.3 in log$_{10}$ and a correlation coefficient of 0.96 (IC95%=[0.85:0.99], p<0.0001) (FIGS. 2 and 3).

Clinical Performance

Clinical performance was evaluated in lab C. All samples from HIV-2-infected patients were validated according to the internal control manufacturer's instructions.

122 to 1,000 ng (median 548 ng) of total DNA per PCR well was analyzed, depending on the total DNA concentration in extracts. HIV-2 DNA was detectable for all 63 patients. HIV-2 DNA was detectable but not quantifiable (<6 copies/PCR) for 20 patients (32%) and quantifiable (≤6 copies/PCR) for 43 patients (68%) with a median HIV-2 DNA load of 2.45 in log$_{10}$ copies/10$^6$ PBMCs (InterQuartile range [IQR]=2.15-3.00 log$_{10}$). For the 20 patients with detectable, but not quantifiable, HIV-2 DNA, the same DNA extracts were retested using 2-6 PCR replicates. Eighteen samples gave positive results in all replicates, one sample had two positive results out of three and one had three positive results out of four, at a level lower than six copies per PCR.

Among the 35 group A samples. HIV-2 DNA was quantifiable in 21 samples (60%), with a median load of 2.56 in log$_{10}$ copies/10$^6$ PBMCs (IQR=2.29-3.03 log$_{10}$). Among the 28 group B samples, HIV-2 DNA was quantifiable in 20 samples (71%), with a median load of 2.27 log$_{10}$ copies/10$^6$ PBMCs (IQR=1.97-2.81 log$_{10}$). There was no difference between groups A and B in the proportion of patients displaying an HIV-2 DNA load below the limit of quantification (p=0.79), nor in the median load (2.56 vs. 2.27 log$_{10}$ copies/10$^6$ PBMCs respectively, p=0.17) when this load was quantifiable.

Among the 18 patients having never received antiretroviral therapy, HIV-2 DNA was quantifiable for 10 of them (56%), with a median load of 2.08 in log$_{10}$ copies/10$^6$ PBMCs (IQR=1.88-2.28 log$_{10}$). Among the 45 antiretroviral-treated patients. HIV-2 DNA was quantifiable in 33 of them (73%), with a median load of 2.60 in log$_{10}$ copies/10$^6$ PBMCs (IQR=2.26-3.09 log$_{10}$). There was no difference in the proportion of patients displaying an HIV-2 DNA load below the limit of quantification between patients having never received antiretroviral therapy and treated patients (p=0.23 for all patients, p=0.74 for group A, and 0.65 for group B). The median HIV-2 DNA load was significantly higher in antiretroviral-treated than in patients having never been treated (p=0.003 for all patients, p=0.068 for group A, and 0.03 for group B), when quantifiable.

Figure 4:
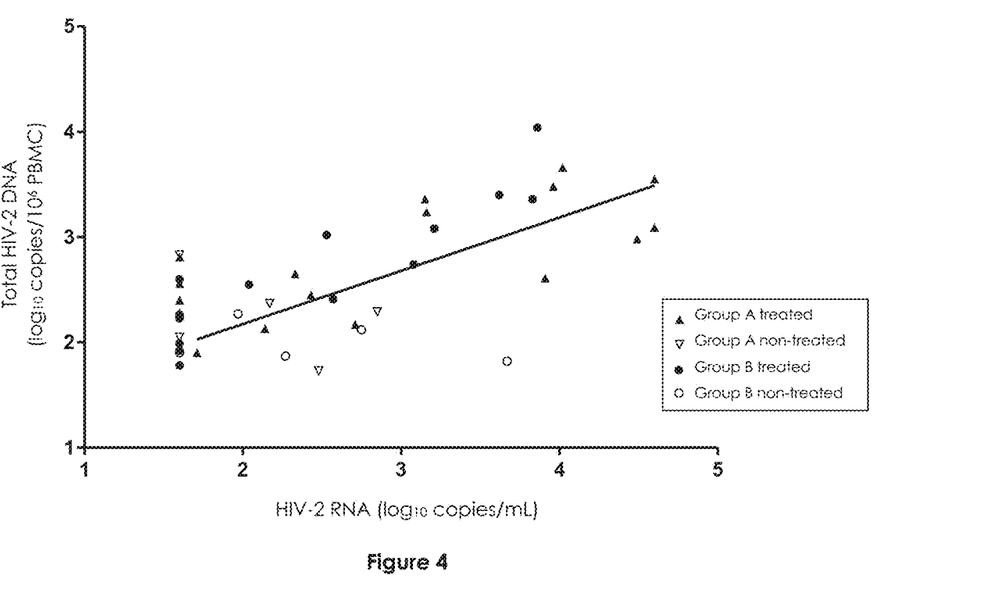
FIGS. 4 and 5
FIGS. 4 and 5 represent the quantity of total HIV-2 DNA (vertical axis, $log_{10}$ of the number of copies for $10^6$ PBMCs) as a function of the quantity of HIV-2 RNA quantity (horizontal axis, in $log_{10}$ of the number of copies per mL (FIG. 3) or of strata of the number of copies per mL (FIG. 4)) for treated group A HIV-2-positive patients (black triangles), non-treated group A HIV-2-positive patients (white triangles), treated group B HIV-2-positive patients (black circles) and non-treated group B HIV-2-positive patients des patients (white circles). An arbitrary value of 1.60 $log_{10}$ copies/mL was attributed to samples with an undetectable plasma viral load.
Figure 5:
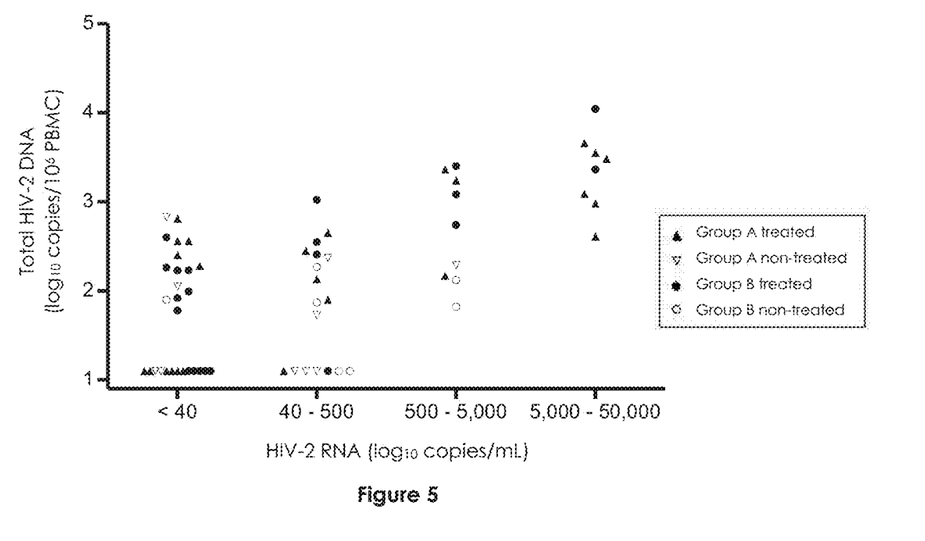

When quantifiable, the HIV-2 DNA load correlated with the HIV-2 RNA load (r=0.68, 95% CI [0.4-0.8], p<0.0001 for the whole group and r=0.73, 95% CI [0.4-0.9], p<0.0002 for treated patients) (FIG. 4). The proportion of patients displaying an HIV-2 DNA load below the limit of quantification was respectively 46%, 39%, 0%, and 0% for an HIV-2 RNA load<40 copies/ml, 40 to 500 copies/ml, 500 to 5,000 copies/ml, and 5,000 to 50,000 copies/ml respectively. When quantifiable, the median (IQR) HIV-2 DNA loads were 2.26 in log$_{10}$ (2.02-2.56 log$_{10}$), 2.37 in log$_{10}$ (2.01-2.50 log$_{10}$), 2.74 in log$_{10}$ (2.17-3.24 log$_{10}$), and 3.42 in log$_{10}$ copies/10$^6$ PBMCs (3.06-3.58 log$_{10}$), respectively (FIG. 5). HIV-2 DNA loads were significantly different depending on the HIV-2 RNA load strata (ANOVA test, p<0.0001). A comparison between subgroups (group A/group B, antiretroviral-treated patients/patients having never been treated) according to HIV-2 RNA load was not relevant because of the small number of patients in each subgroup.

CONCLUSION

Infection by HIV-2 is different from that by HIV-1, especially with respect to its slower progression, therapeutic management, and the level of HIV-2 genetic diversity. Specific molecular methods are therefore necessary for the diagnosis and monitoring of HIV-2 infection (either alone or in the context of a co-infection with HIV-1), the diagnosis of infants born to seropositive HIV-2 mothers, and studying the HIV-2 reservoir. Plasma viremia is undetectable in many HIV-2 infected patients in the absence of antiretroviral therapy, particularly in those with high CD4$^+$ T cell count. HIV-2 DNA may be the only detectable marker in these patients.

The aim of the present invention is thus in particular to develop a highly sensitive quantitative assay for HIV-2 DNA that is easy to implement in developing countries where HIV-2 is endemic.

The detection and quantification method according to the invention exhibits 100% specificity which means the HIV-2 primers did not hybridize to HIV-1 genome. This method also displays good linearity (6 to 6,000 copies/PCR) and good within-PCR reproducibility. The inventors have also shown a good inter-laboratory reproducibility. In addition, the detection and quantification method which may include an external standard for quantification improves reliability and comparisons between different studies. The excellent sensitivity (95% limit of detection: 3 copies/PCR) is useful both for clinical diagnosis and pathophysiological studies.

Both manual and automated extraction methods, as well as two real-time PCR instruments, were validated for compatibility with local practices in resource-limited countries. Eventually, the inventors also showed that the method according to the invention can be performed both on blood cell pellets and on whole blood samples.

The inventors used the same protocol as the Generic HIV DNA Cell® kit (Biocentric. Bandol, France) used to detect and quantify HIV-1 DNA. This test is currently being used with success in many resource-limited countries. This thus facilitates the use of the test according to the invention either for HIV-2 alone or jointly with HIV-1 in the same PCR. This allows for a reduction of analytical costs by increasing the number of samples per PCR and facilitates molecular diagnosis of dual HIV-1/HIV-2 infection within the same sample or diagnosis of HIV infection in babies.

HIV-2 DNA was detectable in blood cells of all patients (infected either with HIV-2 group A or HIV-2 group B): the sensitivity of the method according to the invention has thus been improved relative to previous assays which reported undetectable HIV-2 DNA in 17% (5/29) of samples from HIV-2-infected patients (Damond et al. (2001) *J. Clin. Microbiol.* 39: 4264-4268).

The addition of an internal control, which was absent in the previous assays (Damond et al. (2001) J. Clin. Microbiol. 39: 4264-4268: Gueudin et al. (2005) *Meth. Mol. Biol.* 304: 215-220), allows validating the analytical process.

The inventors also showed that HIV-2-infected patients receiving antiretroviral therapy had higher HIV-2 DNA loads than those of patients having never received antiretroviral treatment, probably because patients who had been treated had more advanced disease, which necessitated the initiation of antiretroviral treatment. Among treated patients, a higher HIV-2 DNA viral load correlated with higher HIV-2 RNA loads, similar to what has been reported for HIV-1 infection (Visseaux et al. (2016) 23*th Conference on Retroviruses and Opportunistic Infections Abstract* 214. Boston, Mass., USA).

Quantification of HIV-2 DNA levels could also provide information about the HIV-2 reservoir, as HIV-1 DNA load has been reported to be a relevant marker of the HIV-1 reservoir. Indeed, the HIV-1 DNA load is predictive of immunological and clinical progression, regardless of CD4+ cell counts and RNA viral load. HIV-1 DNA levels vary depending on the stage of HIV infection, with the highest levels found during primary HIV infection and AIDS. In addition, HIV-1 DNA quantification has allowed reservoir studies in various types of patient cohorts: long-term non-progressors, elite controllers, chronically infected untreated patients, and post-treatment controllers. It has offered a better understanding of the natural history of HIV-1 infection.

In conclusion, the inventors have developed a detection or quantification method (or assay), HIV-2 DNA which has good analytical performance and good clinical sensitivity. This method is particularly successful for both HIV-2 groups A and B, the most prevalent, in comparison with previously described assays (Damond et al. (2001) *J. Clin. Microbiol.* 39: 4264-4268; Gueudin et al. (2008) *AIDS Lond. Engl.* 22: 211-215). The method according to the invention has been validated on a large, well-characterized panel of patient samples. This method is easy to perform assay and is appropriate for use in resource-limited countries in which multiple HIV-2 variants circulate. It can also be particularly useful for HIV-2 diagnosis in babies born to seropositive mothers, for diagnosis of mono- or co-infections with HIV-1, which is important because of monitoring and therapeutic consequences. Eventually, this method is also useful in pathogenesis studies on HIV-2 reservoirs, exploring new insights into the natural history of HIV-2 infection at different stages, and improving opportunities for clinical studies in treated patients.

The invention claimed is:

1. A method for detecting or quantifying deoxyribonucleic acid (DNA) of human immunodeficiency virus 2 (HIV-2) in a sample containing DNA comprising:

a) performing a real-time polymerase chain reaction (PCR) on the sample, or a fraction thereof comprising DNA, with at least two sets of primers and probe each respectively comprising two primers and a labeled probe for the detection or quantification of HIV-2 DNA, at least one of the sets being selected from the group consisting of:

a set comprising a primer comprising or consisting of a sequence SEQ ID NO: 1 or a sequence having at least 90% identity to SEQ ID NO: 1, a primer comprising or consisting of a sequence SEQ ID NO: 2 or a sequence having 90% identity to SEQ ID NO: 2 or the complement of these sequences, and a labeled probe comprising or consisting of a sequence SEQ ID NO: 3, or a sequence having at least 90% identity to SEQ ID NO: 3 or the complement of these sequences, and a set comprising a primer comprising or consisting of a sequence SEQ ID NO: 4 or a sequence having at least 90% identity to SEQ ID NO: 4, a primer comprising or consisting of a sequence SEQ ID NO: 5 or a sequence having 90% identity to SEQ ID NO: 5 or the complement of these sequences, and a labeled probe comprising or consisting of a sequence SEQ ID NO: 6, or a sequence having at least 90% identity to SEQ ID NO: 6 or the complement of these sequences, and b) determining therefrom the presence or absence and/or the quantity of HIV-2 DNA in the biological sample, wherein the primers and probes are each present at a concentration between 300 and 500 nM.

2. The method according to claim 1, wherein in step a) of performing a real-time polymerase chain reaction (PCR) on the sample, or a fraction thereof comprising DNA, is performed with:

(i) at least 4 primers respectively comprising or consisting of:
  a sequence SEQ ID NO: 1 or a sequence having at least 90% identity to SEQ ID NO: 1 or the complement of these sequences, and
  a sequence SEQ ID NO: 2 or a sequence having 90% identity to SEQ ID NO: 2 or the complement of these sequences, and
  a sequence SEQ ID NO: 4 or a sequence having 90% identity to SEQ ID NO: 4 or the complement of these sequences, and
  a sequence SEQ ID NO: 5 or a sequence having 90% identity to SEQ ID NO: 5 or the complement of these sequences, and (ii) at least 2 labelled probes respectively comprising or consisting of:
  a sequence SEQ ID NO: 3, a sequence complement to SEQ ID NO: 3, or a sequence having at least 90% identity to SEQ ID NO: 3 or the complement thereof, and
  a sequence SEQ ID NO: 6, a sequence complement to SEQ ID NO: 6, or a sequence having at least 90% identity to SEQ ID NO: 6 or the complement thereof.

3. The method according to claim 1, wherein the sample containing DNA is a biological sample or a sample comprising cells infected in vitro by HIV-2.

4. The method according to claim 1, wherein the primers respectively consist of SEQ ID NO: 1, SEQ ID NO: 2, SEQ ID NO: 4 and SEQ ID NO: 5, and the labeled probes respectively consist of sequences SEQ ID NO: 3 and SEQ ID NO: 6.

5. The method according to claim 1, wherein the labelled probes are labelled with 6-carboxyfluorescein (FAM) at their 5'end and with Black Hole Quencher-1 (BHQ1) at their 3' end.

6. The method according to claim 1, wherein at least one DNA virus or at least one DNA molecule having essentially no sequence similarity with the genomic sequence of HIV-2 is added to the sample or the fraction thereof, as well as primers and probe necessary for its amplification and detection by real-time PCR, as an internal control of extraction and/or inhibition.

7. The method according to claim 1, wherein the PCR comprises the following thermocycling conditions:
2 min at 50° C., followed by
10 min at 95° C., followed by
50 cycles of 95° C. for 15 s and 60° C. for 1 min.

8. The method according to claim 1, further comprising determining or quantifying HIV-1 nucleic acids in the sample or a fraction thereof.

9. A kit or a mix for detecting or quantifying HIV-2 DNA, comprising:
a) at least two sets of primers and probe each respectively comprising two primers and one probe for the detection or quantification of HIV-2 DNA, the primers and probe being each present at a concentration between 300 and 500 nM, and at least one of the sets being selected from the group consisting of:
   a set comprising a primer comprising or consisting of a sequence SEQ ID NO: 1 or a sequence having at least 90% identity to SEQ ID NO: 1, a primer comprising or consisting of a sequence SEQ ID NO: 2 or the complement of these sequences, and a labelled probe comprising or consisting of a sequence SEQ ID NO: 3, or a sequence having at least 90% identity to SEQ ID NO: 3 or the complement of these sequences, and
   a set comprising a primer comprising or consisting of a sequence SEQ ID NO: 4 or a sequence having at least 90% identity with SEQ ID NO: 4, a primer comprising or consisting of a sequence SEQ ID NO: 5 or a sequence having 90% identity to SEQ ID NO: 5 or the complement of these primers, and a labelled probe comprising or consisting of a sequence SEQ ID NO: 6, or a sequence having at least 90% identity to SEQ ID NO: 6 or the complement of these sequences, and
b) at least one DNA virus or at least one DNA molecule having essentially no sequence similarity with the genomic sequence of HIV-2, as well as primers and probe necessary for its amplification and detection by real-time PCR, as an internal control of extraction and/or inhibition, and
c) optionally additional reagents for performing a PCR.

10. The kit or the mix according to claim 9, comprising:
a1) at least 4 primers, at a concentration between 300 and 500 nm, respectively comprising or consisting of:
   a sequence SEQ ID NO: 1 or a sequence having at least 90% identity to SEQ ID NO: 1 or the complement of these sequences, and
   a sequence SEQ ID NO: 2 or a sequence having 90% identity to SEQ ID NO: 2 or the complement of these sequences, and
   a sequence SEQ ID NO: 4 or a sequence having 90% identity to SEQ ID NO: 4 or the complement of these sequences, and
   a sequence SEQ ID NO: 5 or a sequence having 90% identity to SEQ ID NO: 5 or the complement of these sequences, and
a2) at least 2 labelled probes at a concentration between 300 and 500 nM, respectively comprising or consisting of:
   a sequence SEQ ID NO: 3, a sequence complement to SEQ ID NO: 3, or a sequence having at least 90% identity to SEQ ID NO: 3 or the complement thereof, and
   a sequence SEQ ID NO: 6, a sequence complement to SEQ ID NO: 6, or a sequence having at least 90% identity to SEQ ID NO: 6 or the complement thereof.

11. The kit or the mix according to claim 9, further comprising primers and at least one labelled probe for detecting or quantifying HIV-1 nucleic acids.

12. An in vitro method for determining HIV-2 viral load, in an individual, comprising the steps of:
(c) performing the method for detecting or quantifying HIV-2 DNA in a biological sample taken from the individual as defined in claim 1; and
(d) determining therefrom the HIV-2 viral load of the individual.

* * * * *